(12) United States Patent
Maseda

(10) Patent No.: US 6,514,237 B1
(45) Date of Patent: Feb. 4, 2003

(54) CONTROLLABLE INTRALUMEN MEDICAL DEVICE

(75) Inventor: Luis J. Maseda, Newport Beach, CA (US)

(73) Assignee: Cordis Corporation, Miami Lakes, FL (US)

( * ) Notice: Subject to any disclaimer, the term of this patent is extended or adjusted under 35 U.S.C. 154(b) by 57 days.

(21) Appl. No.: 09/706,680

(22) Filed: Nov. 6, 2000

(51) Int. Cl.$^7$ .............................................. A61M 25/16
(52) U.S. Cl. ...................... 604/533; 604/264; 604/523; 414/1
(58) Field of Search ................... 604/533, 158, 604/171, 177, 264, 265, 266, 523, 104, 8, 531, 20; 623/24, 25, 64; 414/1, 7

(56) References Cited

U.S. PATENT DOCUMENTS

| | | | |
|---|---|---|---|
| 4,543,090 A | | 9/1985 | McCoy .......................... 604/95 |
| 4,753,223 A | | 6/1988 | Bremer ........................... 128/4 |
| 5,268,082 A | * | 12/1993 | Oguro et al. .................. 604/20 |
| 5,295,979 A | * | 3/1994 | DeLaurentis et al. ........ 604/265 |
| 5,370,615 A | | 12/1994 | Johnson ........................ 604/96 |
| 5,443,497 A | | 8/1995 | Venbrux ......................... 623/1 |
| 5,538,510 A | | 7/1996 | Fontirroche et al. ......... 604/265 |
| 5,716,410 A | * | 2/1998 | Wang et al. ................. 604/531 |
| 5,728,068 A | | 3/1998 | Leone et al. ................. 604/101 |
| 5,795,318 A | * | 8/1998 | Wang et al. ..................... 604/8 |
| 5,800,421 A | | 9/1998 | Lemelson ................. 604/891.1 |
| 5,820,594 A | | 10/1998 | Fontirroche et al. .......... 604/96 |
| 5,855,565 A | * | 1/1999 | Bar-Cohen et al. .......... 604/104 |
| 5,885,258 A | | 3/1999 | Sachdeva et al. ............ 604/281 |
| 6,109,852 A | * | 8/2000 | Shahinpoor et al. ............ 414/1 |
| 6,273,875 B1 | * | 8/2001 | Siman et al. ................ 604/264 |
| 6,379,393 B1 | * | 4/2002 | Mavroidis et al. ............ 623/25 |

OTHER PUBLICATIONS

M. Shahinpoor, Y.Bar–Cohen, T. Xue, J.O. Simpson and J. Smith "Ionic Polymer–Metal Composites (IPMC) As Biomimetic Sensors and Actuators"; Proceedings of SPIE's 5th Ann Int'l Symposium on Smart Structures and Materials, Mar. 1–5, 1998, San Diego, CA; Paper No. 3324–27.

Chang Liu and Y. Bar–Cohen "Scaling Laws of Microactuators and Potential Applications of Electroactive Polymers in MEMS"; Proceedings of SPIE's 6$^{th}$ Annual International Symposium on Smart Structures and Materials, Mar. 1–5, 1999, Newport Beach, CA; Paper No. 3669–33.

C. Liu, Y. Bar–Cohen, and s. Larry "Electro–statically stricted polymers (ESSP)"; Proceeedings of SPIE's 6$^{th}$ Annual International Symposium on Smart Structures and Materials, Mar. 1–5, 1999, Newport Beach, CA ; Paper No. 3669–41.

Y. Bar–Cohen, T. Xue, B. Joffe, S.–S. Lih, M. Shahinpoor, J. Simpson, J. Smith and P. Willis; "Electroactive Polymers (EAP) Low Mass Muscle Actuators"; Presented at the SPIE International Conference, Smart Structures and Materials Symposium, Enabling Technologies: Smart Structures and Integrated Systems, San Diego, CA, Mar. 3–6, 1997.

(List continued on next page.)

Primary Examiner—Teresa Walberg
Assistant Examiner—Fadi H. Dahbour
(74) Attorney, Agent, or Firm—Carl J. Evems

(57) ABSTRACT

An intralumen medical device which incorporates electroactive polymer actuators into various sections of flexible medical probes results in a device capable of precisely navigating through tortuous passageways. Electroactive polymer actuators can be attached to or replace various sections of flexible medical probes and selectively activated via a controller to produce various coordinated movements or states of rigidity in the flexible medical probe.

7 Claims, 11 Drawing Sheets

OTHER PUBLICATIONS

M. Shahinpoor "Electro–Mechanics of Iono–Elastic Beams as Electrically–Controllable Artificial Muscles"; Artificial Muscle Research Institute, School of Engineering & School of Medicine, University of New Mexico, Albuquerque, New Mexico 87131.

M. Shahinpoor, Y. Bar–Cohen, J.O. Simpson and J. Smith, "Ionic Polymer–Metal Composites (IPMC) as Biomimetic Sensors, Actuators & Artificial Muscles—A Review"—Artificial Muscles Research Institute, Univ. of New Mexico, NASA Jet Propulsion Laboratory (JPL), California Institute of Technology, Pasadena, CA; Composites and Polymers Branch, NASA Langley Research Center, Hampton, VA 23681–0001.

* cited by examiner

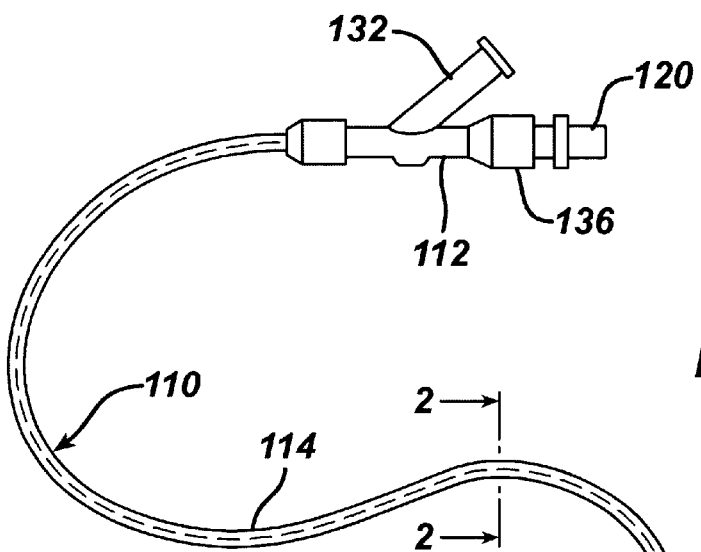
FIG. 1
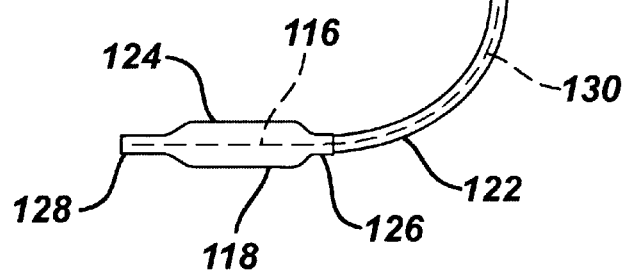
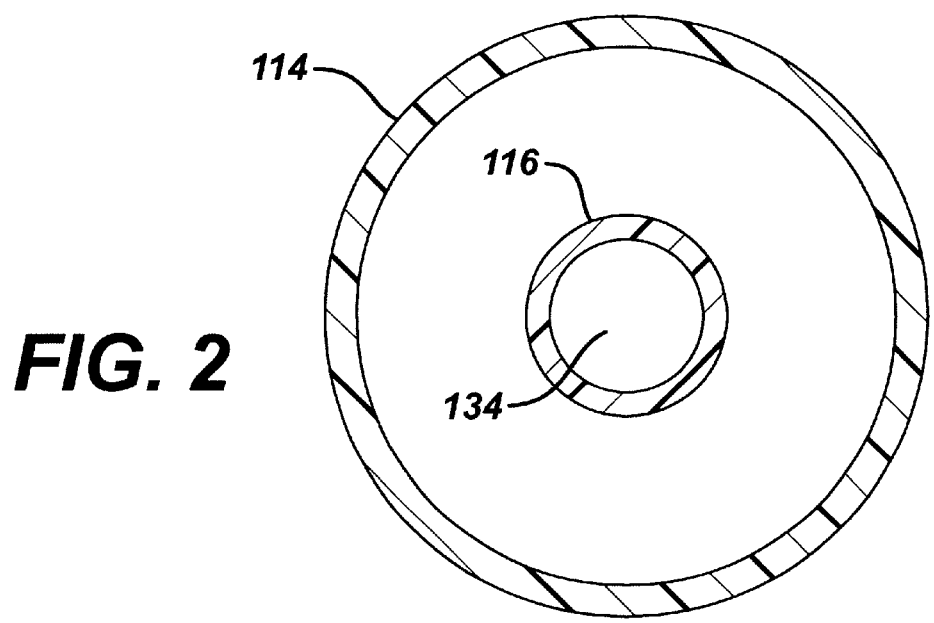
FIG. 2

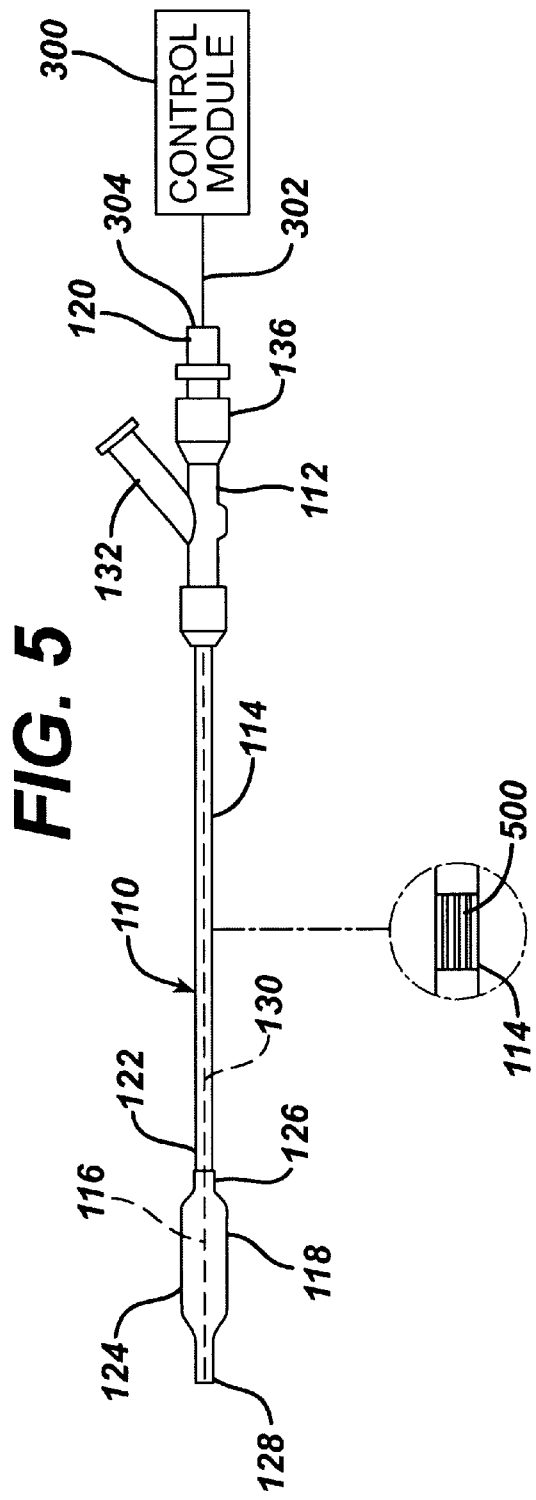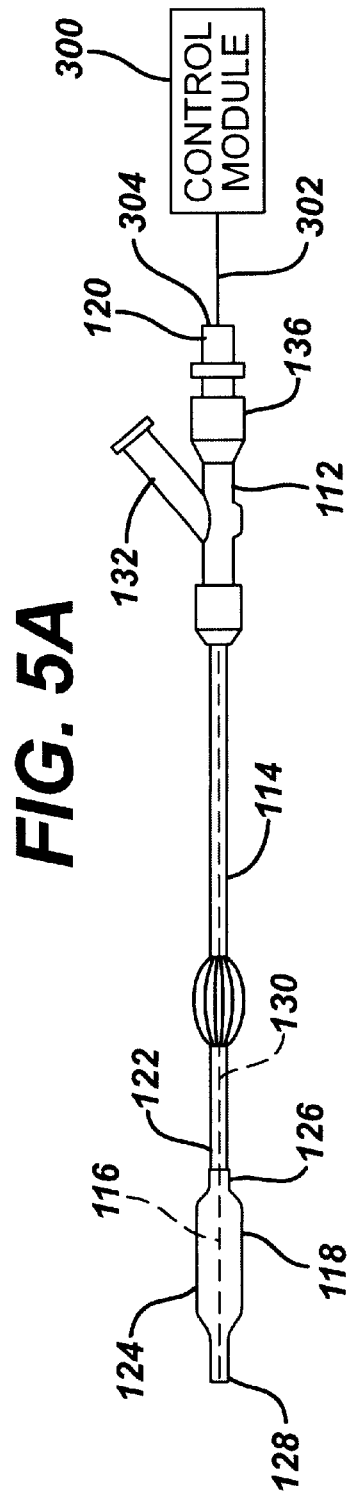

CONTROLLABLE INTRALUMEN MEDICAL DEVICE

BACKGROUND OF THE INVENTION

1. Field of the Invention

The present invention relates to medical devices, and more particularly to catheters, cannulae, guidewires, endoscopes and similar flexible probe devices incorporating electroactive polymers for increased maneuverability and controllability.

2. Discussion of the Related Art

Coronary balloon angioplasty catheters are widely used in surgical operations for dilating blocked or clogged arteries. Such catheters utilize inflatable balloons, which are implanted at the site of a blockage in an uninflated state and are then inflated. The inflated balloon presses the blockage against the vascular wall in order to diminish the volume of the blockage and dilate the artery for reestablishing a more healthful blood flow. An intraluminal stent may then be implanted into the artery in order to permanently support the region that has been repaired by the angioplasty. A conventional method of stent deployment includes disposing the stent in a collapsed state above a deflated angioplasty balloon, inserting the balloon and stent into the vessel and inflating the balloon in order to expand the stent.

One concern with this device and similar devices is their flexibility and steerability, characteristics which significantly bear on the ease with which the device can be introduced and passed through the various channels of the body.

Accordingly, attempts have been made to produce a catheter, cannula, endoscope, or the like, which is readily insertable and manipulable for ease of advancement through body cavities or channels. One such device is disclosed in U.S. Pat. No. 4,543,090. U.S. Pat. No. 4,543,090 discloses a catheter comprising a tubular member having a proximal end and a distal end for insertion into the body. The distal end comprises a plurality of interconnected temperature activated memory elements. The memory elements are interconnected in such a way as to provide coordinated movement of the distal end. Essentially, each memory element assumes a first shape when heated to a predetermined temperature and a second shape in response to a force produced by one element acting upon an interconnected element. The memory elements are coupled to a controller for deflecting the distal end of the catheter in a plurality of directions to steer or aim it within the body.

U.S. Pat. No. 4,753,223 discloses a catheter assembly comprising an elongated, flexible, tubular body having a proximal end for connection to a power source and a distal end for insertion into a body. Rigid rings encircle the tubular body at axially spaced locations along the distal end. A plurality of shape memory wires extend between adjacent rings and are electrically connected to a control device and power source. By passing an electrical current through the wires in a controlled sequence, the tubular body may be steered through the body.

While each of these devices offers some degree of steerability, they do not provide for the coordinated precision movements required for a high degree of maneuverability.

Other attempts to provide catheters having distal ends, which, when inserted into a body are manipulable to advance the catheter through body cavities, include the devices disclosed in U.S. Pat. Nos. 3,674,014 and 3,773,034. U.S. Pat. No. 3,674,014 discloses a catheter that includes permanent magnets and employs a magnetic field to bend the distal end of the catheter. U.S. Pat. No. 3,773,034 discloses a catheter that includes fluid conduits and employs a fluid to bend the distal end of the catheter. Although these devices are steerable, they are somewhat difficult to control and manipulate.

Other work has focused on producing a catheter which is readily insertable while being effectively anchorable in a body cavity. For example, in U.S. Pat. No. 3,890,977, a catheter is disclosed in which the distal end is formed into a desired shape by using a material exhibiting mechanical memory that is triggered by heat. By heating the mechanical memory material, the distal end of the catheter is shaped to anchor the catheter within the body. However, the change in shape of the distal end in this device is essentially limited to a single direction.

SUMMARY OF THE INVENTION

The controllable intralumen medical device of the present invention provides a means for overcoming the difficulties associated with the use and operation of the devices as briefly described above.

In accordance with one aspect, the present invention is directed to a controllable intralumen medical device. The medical device comprises a flexible medical probe having one or more integral electroactive polymer actuators and a control module coupled to the flexible medical probe for selectively controlling the one or more electroactive polymer actuators.

In accordance with another aspect, the present invention is directed to a method for controlling the movement of an intralumen medical device. The method comprises integrating one or more electroactive polymer actuators into the intralumen medical device at one or more predetermined locations and selectively controlling the one or more electroactive polymer actuators to cause specific movements and states of rigidity in the intralumen medical device.

The controllable intralumen medical device of the present invention integrates a controller and electroactive polymers with flexible probe medical devices such as catheters, guidewires, cannulae and endoscopes to create a device capable of navigating through tortuous passages where precise control of the device is desired. By configuring the electroactive polymer material (typically strands) in various schemes and synchronizing material activation via the controller, the potential movement of the flexible probe that can be achieved would essentially be limitless. The combination of strand length, placement in or on the flexible probe, size and level of activation will determine the amount and type of movement possible. For example, the device may be made to bend in any direction in three-dimensional space. In addition, specific movements or states of rigidity may be achieved. For example, the device may be made to wiggle, slither, twirl, pulse, vibrate, rotate, expand or virtually be made to make any other movement or combination of movements. The device may also be made rigid along its entire length or in sections such that it may be guided through difficult to pass regions such as regions having tight stenotic lesions.

The electroactive polymer strands may be incorporated into or replace any portion of the flexible probe medical devices, including the tips, inner body, outer body or any other component of the devices to develop smart devices that can be controlled with a high degree of precision. In addition to making the device highly maneuverable as described above, the electroactive polymer strands may be integrated into various segments of the devices such that a section of the device expands in a manner which mimics a balloon in a balloon catheter or to expand an end of the probe to mimic an anchoring device.

BRIEF DESCRIPTION OF THE DRAWINGS

The foregoing and other features and advantages of the invention will be apparent from the following, more particular description of preferred embodiments of the invention, as illustrated in the accompanying drawings.

FIG. 1 is a perspective view of an exemplary balloon catheter in accordance with the present invention.

FIG. 2 is an enlarged cross-sectional view of the catheter of FIG. 1, along line 2—2.

FIGS. 5 and 5A are perspective views of a fourth exemplary embodiment of the controllable intralumen medical device in accordance with the present invention.

DETAILED DESCRIPTION OF THE PREFERRED EMBODIMENTS

Figure 3:
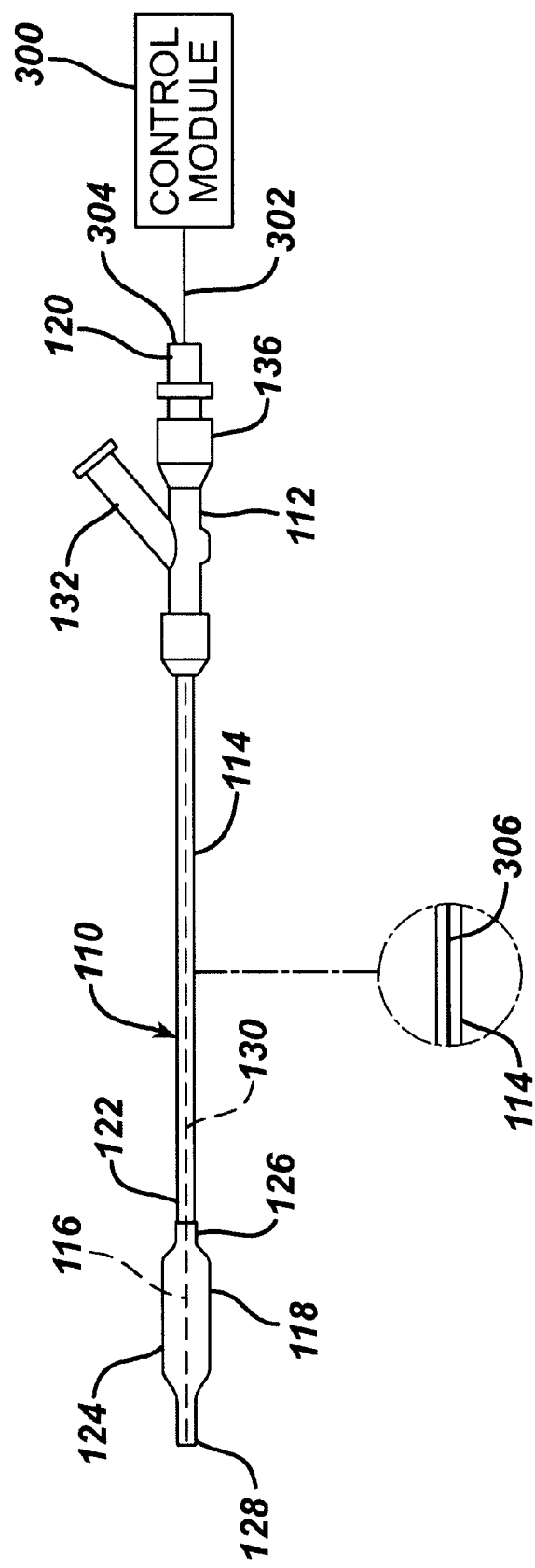
FIGS. 3 and 3A are perspective views of a first exemplary embodiment of the controllable intralumen medical device in accordance with the present invention.

The controllable intralumen medical device of the present invention comprises a flexible medical probe device having strategically embedded electroactive polymer strands, and a controller. Specific movements and/or states of rigidity in the flexible probe device may be achieved by selective activation, via the controller, of the electroactive polymer strands arranged in various configurations. The activation, via the controller, of the electroactive polymer strands embedded in and/or replacing sections of the flexible probe device may induce movements such as wiggling, slithering, twirling, bending, pulsing, vibrating, rotation, expansion, contraction or elongation. The static states may induce various levels of rigidity throughout the flexible probe device or hold the flexible probe device in a certain shape. The electroactive polymer strands may be embedded in any type of flexible medical probe device, including catheters, cannulae, guidewires and endoscopes. Although the electroactive polymer strands may be utilized in conjunction with any type of device, for ease of explanation, the exemplary embodiments described below will be with reference to a balloon catheter.

Referring to the drawings, FIGS. 1 and 2 illustrate an exemplary embodiment of a balloon catheter 110. The balloon catheter 110 comprises a Y-connector or hub 112, a catheter shaft including an outer tubular shaft 114 and an inner tubular shaft 116, and a dilation balloon 118. The hub 112 is disposed at the proximal end 120 of the balloon catheter 110 and the balloon 118 is disposed at the distal end 122 of the balloon catheter 110. The balloon 118 may be formed from a flexible, substantially inelastic material having a cylindrical dilation section 124 as well as proximal and distal legs 126, 128 respectively. The outer tubular shaft 114 is coupled to the hub 112 at the proximal end 120 of the balloon catheter 110 and to the proximal leg 126 of the balloon 118 at the distal end 122 of the balloon catheter 110. The outer tubular shaft 114 terminates at the point where it is sealed to the proximal leg 126 of the balloon 118. The outer surface of the outer tubular shaft 114 may be treated with any suitable coating to improve the performance of the balloon catheter 110. For example, the outer surface may be treated with a hydrophilic coating.

The inner tubular shaft 116 extends through the interior of the outer tubular shaft 114, thereby defining a generally annular space or inflation lumen 130 between the outer tubular shaft 114 and the inner tubular shaft 116. The hub 112 comprises an inflation port 132, which is in fluid communication with the inflation lumen 130 at the proximal end 120 of the balloon catheter 110. The inflation lumen 130 extends from where it is in fluid communication with the inflation port 132, along the entire length of the outer tubular shaft 114, and terminates in fluid communication with the interior of the balloon 118. The inner tubular shaft 116 extends from the hub 112 through the length of the outer tubular shaft 114 and through the interior of the balloon 118 where it is sealed to the distal leg 128 such that a guidewire lumen 134, defined by the inner tubular body 116, remains open. The hub 112 also comprises a guidewire port 136, which communicates with the guidewire lumen 134 to enable fluid communication throughout the entire length of the balloon catheter 110. A guidewire, not illustrated, may thus be easily advanced and withdrawn through the guidewire lumen 134 of the balloon catheter 110 to assist in directing the distal end 122 into selected vessels or to temporarily provide greater stiffness or support to the catheter shafts.

Electroactive polymers may be incorporated into one or more sections of the balloon catheter 110 illustrated in FIGS. 1 and 2. While there are a number of different classes of electroactive polymers, for ease of explanation, exemplary embodiments of the present invention will be described with respect to one particular type of electroactive polymer; namely, ion-exchange polymer- noble metal composites. Ion-exchange polymer-noble metal composites are large motion actuators that operate under a low voltage compared to other actuators, such as piezoceramics or shape metal alloys. Ion-exchange polymer-noble metal composites are simple, lightweight strips of highly flexible plastic that bend and function similarly to human fingers when an electric voltage is applied thereto. Essentially, strips of these composites undergo large bending and flapping displacement when an electric field is applied.

While other materials may be utilized in conjunction with flexible medical probe devices, for example, hydrogels, electroactive polymers and specifically ion-exchange polymer-noble metal composites are preferred because of their unique characteristics. Ion-exchange polymer-noble metal composites are low density, high toughness, large activation strain constant materials that exhibit inherent vibration damping and have easily tailorable properties. Essentially, ion-exchange polymer-noble metal composites may be manufactured and cut into any shape and size.

Ion-exchange polymer-noble metal composites are manufactured utilizing a chemical process in which a noble metal is deposited within the molecular network of the base ionic polymer. Metal ions, for example, platinum are dispersed throughout the hydrophilic regions of the polymer and subsequently chemically reduced to the corresponding metal atoms. This process results in the formation of dendritic-type electrodes. When an external voltage of approximately 2 volts or higher is applied to an ion-exchange polymer-noble metal composite film, it bends toward the anode. An increase in the applied voltage, up to a predetermined limit, causes a larger bending displacement. When the polarity of the voltage is changed, the film undergoes a swinging movement. The displacement of the film not only depends on the magnitude of the applied voltage, but also on the frequency of the applied voltage. Lower frequencies lead to higher displacements. Accordingly, the movement of the film or strip may be fully controllable by controlling the applied voltage.

As stated above, strips or strands of ion-exchange polymer-noble metal composites may be integrated into one or more sections of a flexible medical probe device, for example, a balloon catheter. If, however, hydrogels were to be utilized, the hydrogels would be inserted into chambers in one or more locations in the flexible medical probe device. Referring to FIG. 3, there is illustrated one exemplary embodiment of the present invention. A controller or control module 300 may be coupled to the balloon catheter 110 in any number of ways, including via an electrical conduit 302. The electrical conduit 302 extends from the control module 300 to the one or more strands of composite via a conduit access port 304 in the hub 112 of the balloon catheter 110. Although not illustrated, the wires forming the electrical conduit 302 may be connected to the composite strands in any suitable manner, including utilizing chemical and/or mechanical bonding techniques. For example, the wires may be bonded to the composite strands utilizing adhesives or solder. In an alternate embodiment, the control module 300 may be integrally formed with the hub 112 thereby eliminating the need for an external conduit.

The control module 300 preferably comprises a power supply capable of supplying both DC voltage/current and AC voltage/current at various frequencies. The power supply may comprise circuitry to convert external sources of power into the desired output, it may comprise internal sources of power, and/or it may comprise both sources of power. For example, the primary source of power may be provided from an external source, and back-up power may be provided from internal sources, such as batteries. The control module 300 preferably also comprises the circuitry/logic for precisely controlling the output signals from the control module 300 to the composite strands and for monitoring the feedback signals from the composite strands. The control laws for the control module 300 may be developed utilizing well known techniques.

Figure 3A:
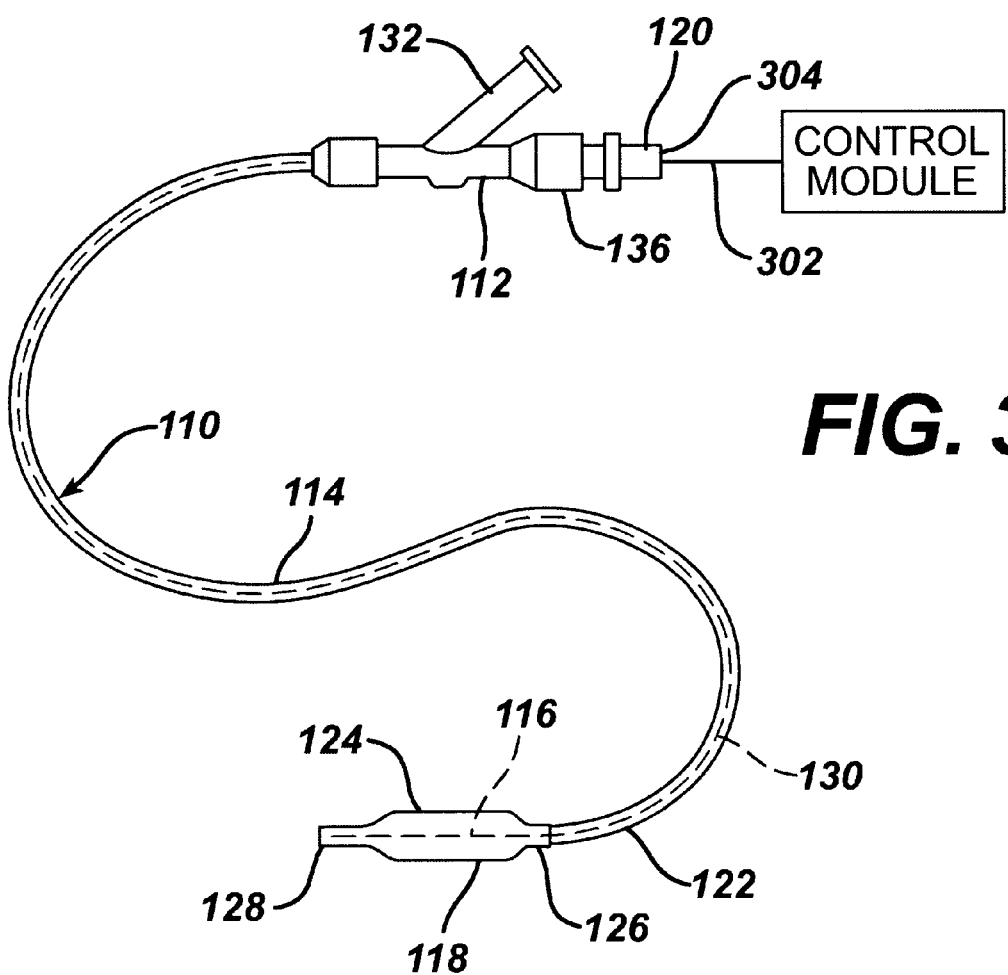
Figure 3B:
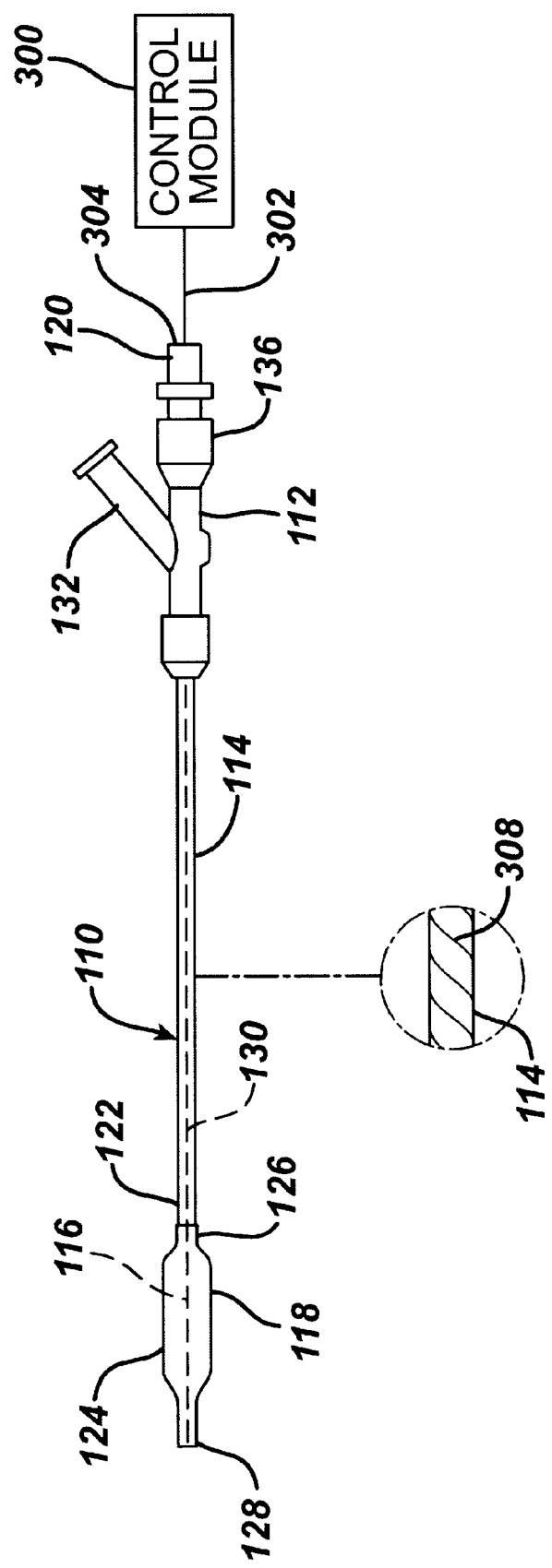
FIG. 3B is a perspective view of a second exemplary embodiment of the controllable intralumen medical device in accordance with the present invention.

In this exemplary embodiment, a composite strand 306 is attached to the outer tubular body 114 along substantially its entire length. The composite strands may be attached to the outer tubular body 114 in any suitable manner and utilizing any suitable chemical or mechanical means, including placement in extruded grooves in the outer tubular body 114, bonded to the surface of the outer tubular body 114 utilizing adhesives, or force fit utilizing a tongue and groove arrangement. When no voltage is applied across the composite strand 306, the composite strand 306 is pliable and soft and the outer tubular body 114 is capable of easily bending as illustrated in FIG. 3. When a predetermined voltage is applied across the composite strand 306, the composite strand 306 becomes rigid and pushable and the outer tubular body 114 also becomes pushable as illustrated in FIG. 3A. In an alternate embodiment, the same effect as described above may be achieved by wrapping the entire outer tubular body 114 with a single composite strand 308 in a helical manner as illustrated in FIG. 3B. In another alternate embodiment, multiple composite strands may be incorporated into selected sections of the outer tubular body 114 and selectively activated such that some sections remain pliable and soft and other sections become rigid and pushable. In this manner, a high degree of steerability may be achieved. For example, in the situation where an artery is blocked with tight stenotic lesions and those blockages are in a curved area of the artery, the tip of the catheter 110 may be made soft and pliable while an adjacent portion may be made rigid, thereby providing steerability via the tip and pushability via the adjacent portion.

Figure 4:
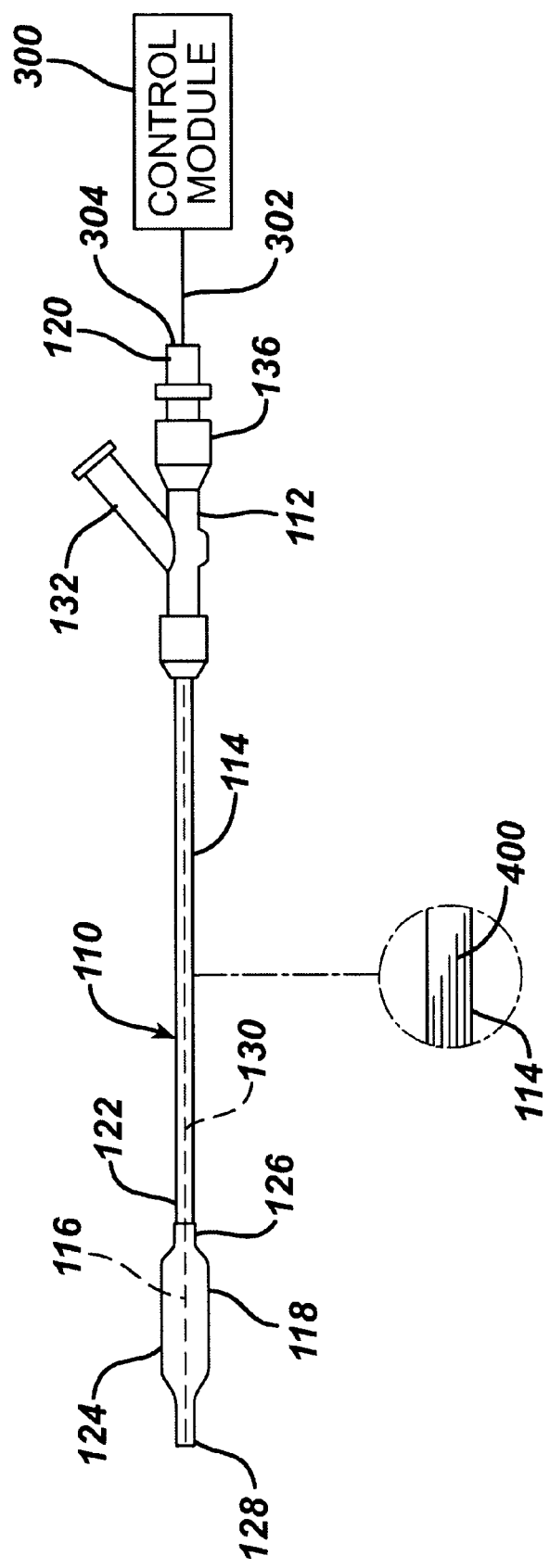
FIGS. 4 and 4A are perspective views of a third exemplary embodiment of the controllable intralumen medical device in accordance with the present invention.
Figure 4A:
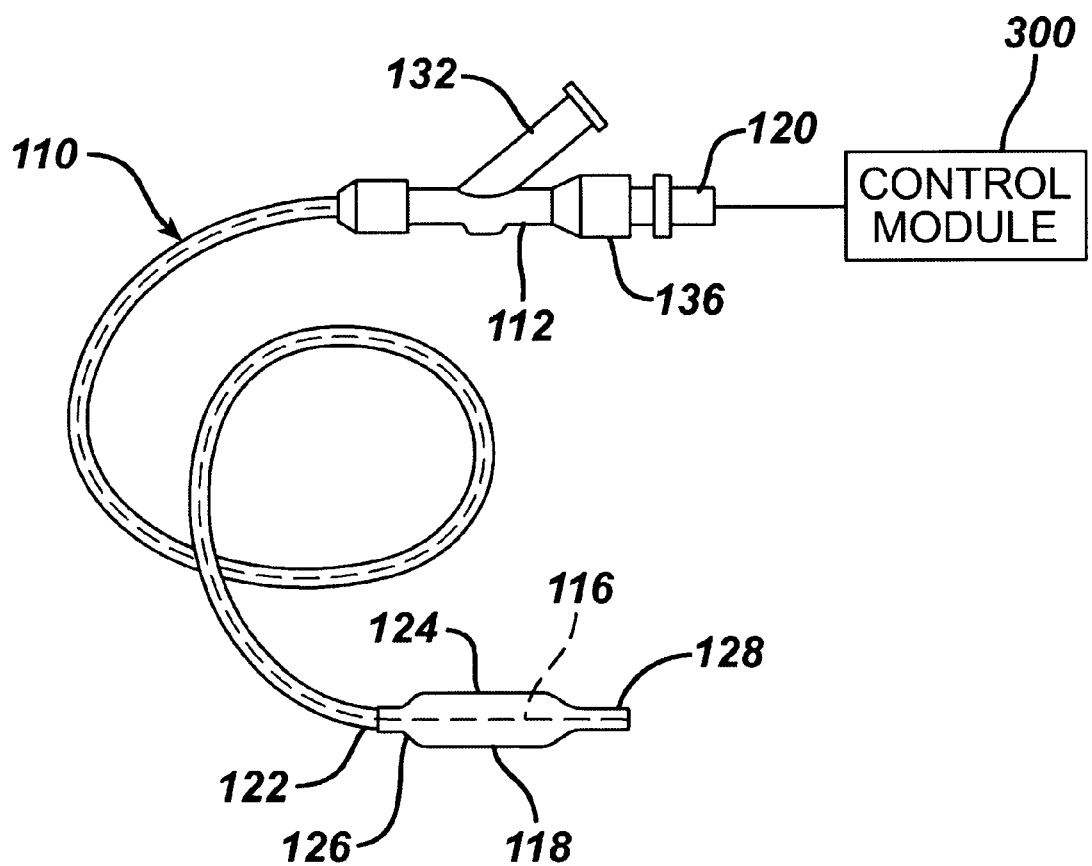

FIG. 4 illustrates another exemplary embodiment of the present invention. In this exemplary embodiment, multiple composite strands 400 are attached to the outer tubular body 114 in a staggered or stair step configuration. The composite strands 400 may be attached to one section or to multiple sections of the outer tubular body 114 of the balloon catheter 110. The multiple composite strands 400 may be attached in any suitable manner as described above. By having the composite strands 400 of differing lengths arranged circumferentially around the outer tubular body 114, the outer tubular body 114 may be made to bend or twist back on itself in a pretzel-like manner. When no voltage is applied to the composite strips 400, the outer tubular body 114 holds its normally relaxed position as illustrated in FIG. 4. However, when a predetermined voltage is applied to the composite strips 400 in a controlled manner, via the control module 300, the outer tubular body 1 14 and thus the balloon catheter 110 itself may be made to bend as illustrated in FIG. 4A.

In yet another exemplary embodiment, one or more sections of the outer tubular body 114 may be removed entirely and replaced with circumferentially spaced composite strands 500 as illustrated in FIG. 5. The composite strands 500 may be attached to the ends of the sections of the outer tubular body 1 14 by any suitable means such as chemical or mechanical bonding as briefly described above. When no voltage is applied to the composite strips 500, the outer tubular body 114 holds its normally relaxed position as illustrated in FIG. 5. However, when a predetermined voltage is applied to the composite strips 500 in a controlled manner, via the control module 300, the composite strips 500, which are constrained from movement on their ends, expand like a balloon as illustrated in FIG. 5A. Because the level of activation for each strip 500 may be independently controlled, the size and shape of the balloon may be varied. For example, non-symmetrical or asymmetrical pressure may be applied by varying the degree of activation for one or more of the composite strips 500. This type of composite strand configuration may be placed at any location in the outer tubular body 114 and may be used any number of times to expand difficult-to-pass passageways. In addition, this configuration may be placed at more than one location in the outer tubular body 114, and each location may be independently controlled.

Figure 6:
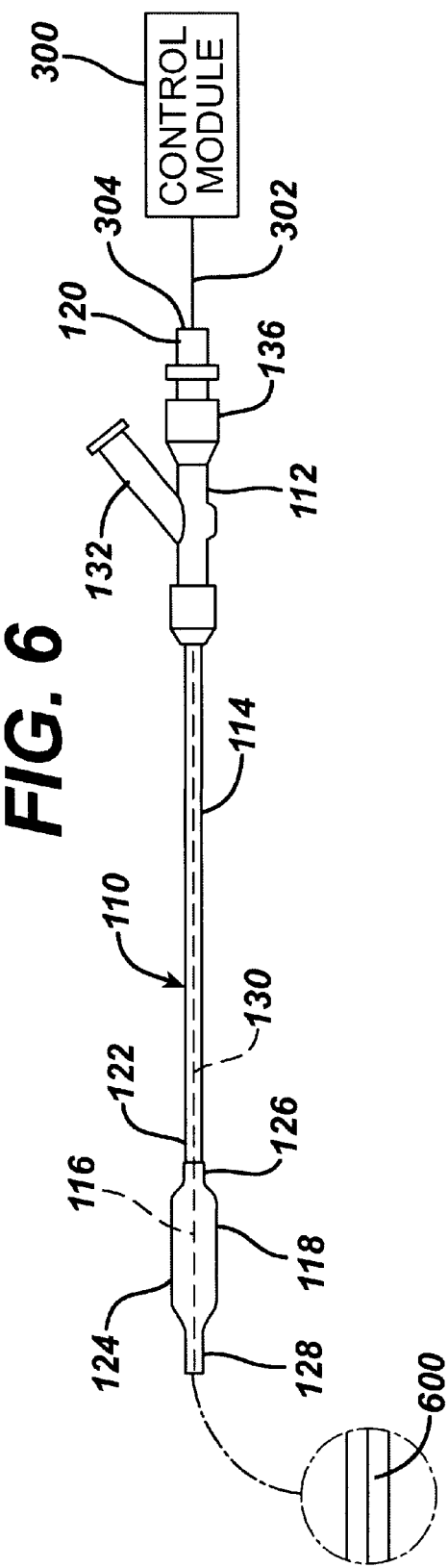
FIGS. 6 and 6A are perspective views of a fifth exemplary embodiment of the controllable intralumen medical device in accordance with the present invention.
Figure 6A:
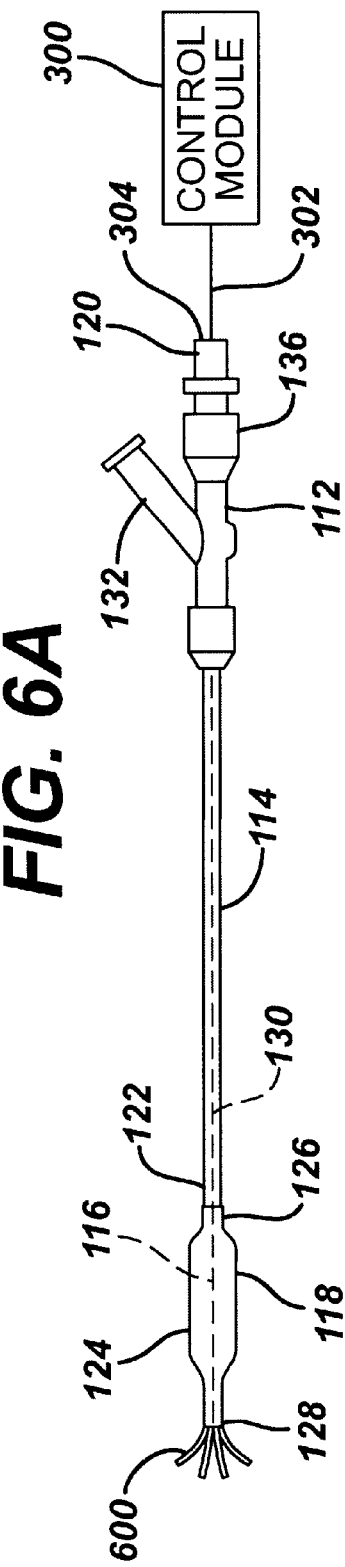

FIG. 6 illustrates another exemplary embodiment of the present invention. In this exemplary embodiment, the composite strands 600 may be attached to the end of the distal leg 128 of the balloon 118 of the balloon catheter 110. The composite strands 600 may be attached to the distal leg 128 in any suitable manner as briefly described above. The composite strands 600 are arranged circumferentially in a manner similar to that described with respect to the embodiment illustrated in FIG. 5, except that the strands are only attached on one end. When no voltage is applied to the composite strips 600, the composite strips 600 simply form an extension of the distal leg 128. However, when a predetermined voltage is applied to the composite strips 600 in a controlled manner, via the control module 300, the composite strips 600, which are only constrained from movement on one end rather than both ends, simply peel away in a manner similar to the way skin is peeled from a banana as illustrated in FIG. 6A. In this configuration, the balloon catheter 110 may be anchored into position during a particular procedure. Because the level of activation for each strip 600 may be independently controlled, individual strips may be made to bend as illustrated in FIG. 6A. In addition, by reversing the polarity of the applied voltage one or more of the composite strips may be made to bend inwardly as opposed to outwardly. Since independent activation is available, various combinations of composite strip movement may be achieved.

Figure 7:
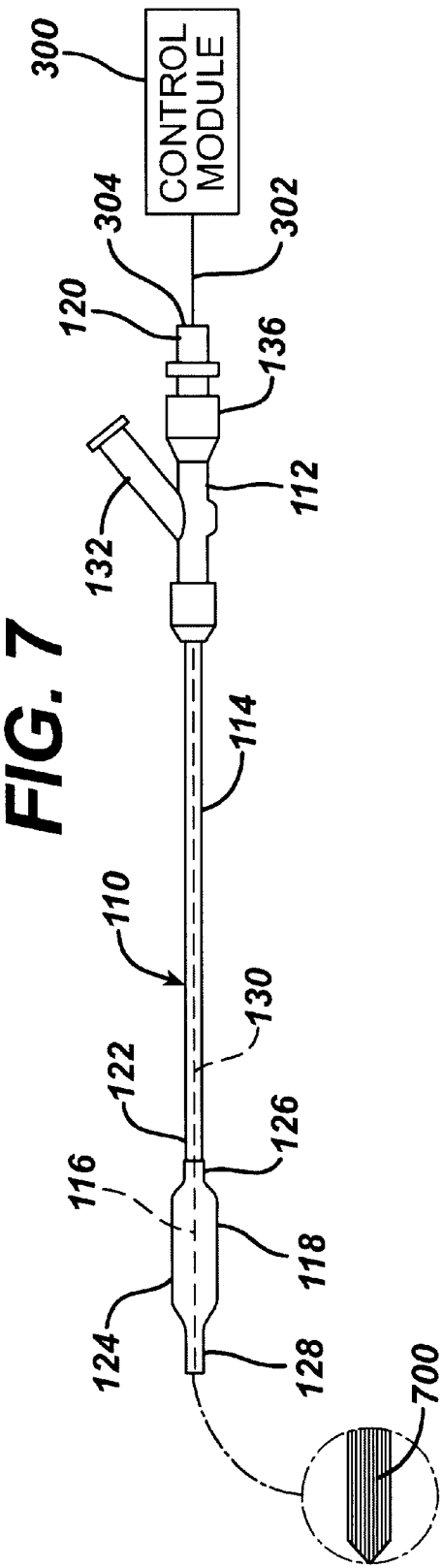
FIGS. 7, 7A and 7B are perspective views of a sixth exemplary embodiment of the controllable intralumen medical device in accordance with the present invention.
Figure 7A:
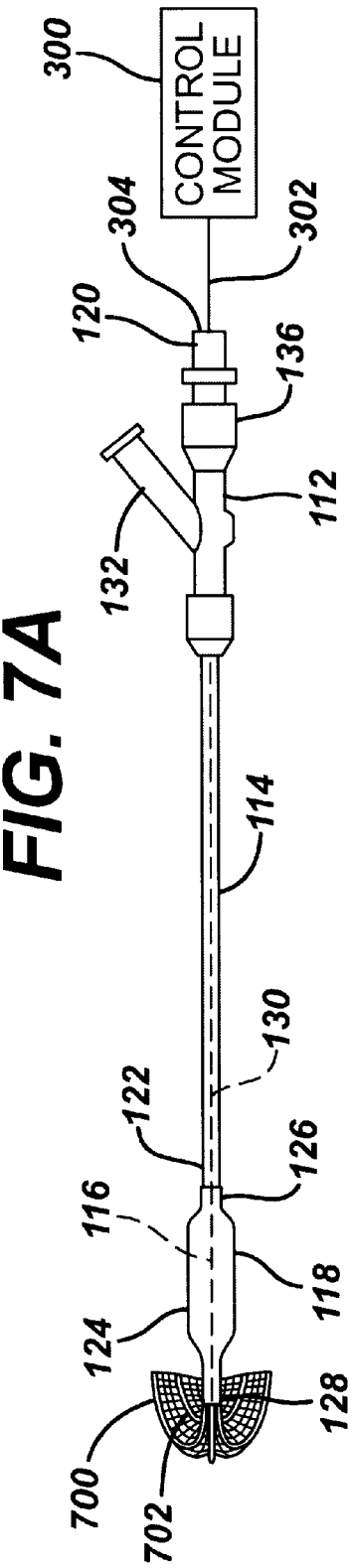
Figure 7B:
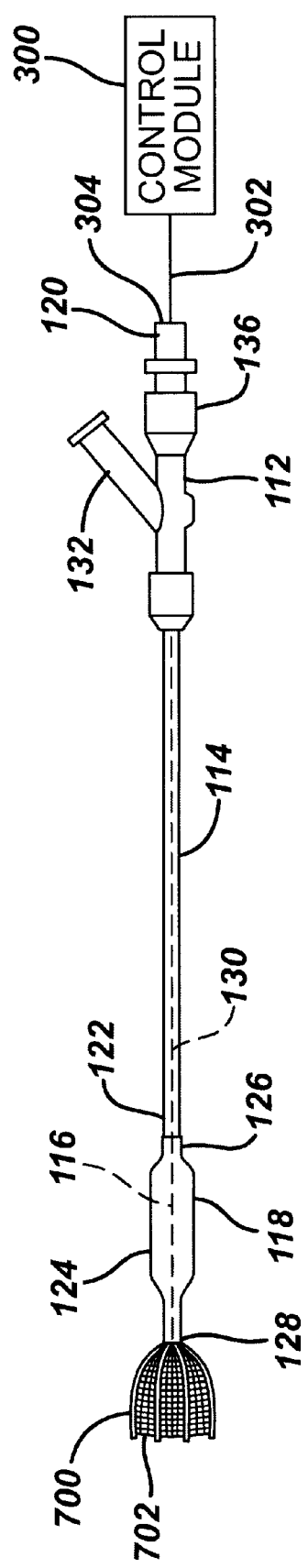

In an alternate embodiment, the composite strips may be attached to the end of the distal leg 128 of the balloon 118 in a manner similar to that described above with respect to FIG. 6, but instead of allowing each strip to act independently, they may be constrained to act in concert. FIG. 7 illustrates an exemplary embodiment wherein the composite strips 700 are constrained to work in concert. In this embodiment, the composite strips 700 are interconnected along their length by a mesh material 702. The mesh material may be any biocompatible material, such as nylon, which does not substantially interfere with fluid flow. In other words, fluids should be able to readily pass therethrough. Accordingly, when no voltage is applied to the composite strips 700, the composite strips 700 and the interconnecting mesh 702 simply form an extension of the distal leg 128. However, when a predetermined voltage is applied to the composite strips 700, the composite strips 700, which are constrained from movement on one end and along their lengths by the mesh 702, open in a funnel or umbrella-like manner as illustrated in FIG. 7A. With this configuration, the distal end of the balloon catheter 110 may be utilized as a clot catcher or for similar purposes. For example, the funnel may be formed by activating the composite strips 700 in a controlled manner to catch a clot or other foreign matter depending on mesh pore size, and once the clot or other foreign matter is collected, the composite strips 700 may be deactivated or the polarity reversed, thereby collapsing the funnel and securely holding the clot or other foreign matter until the flexible probe is removed. The mesh material 702 may be attached to the composite strips 700 utilizing any suitable means such as mechanical or chemical bonding techniques including adhesives. In another exemplary embodiment, the composite strips 700 and mesh 702 may be configured to open in the opposite direction as illustrated in FIG. 7B.

Figure 8:
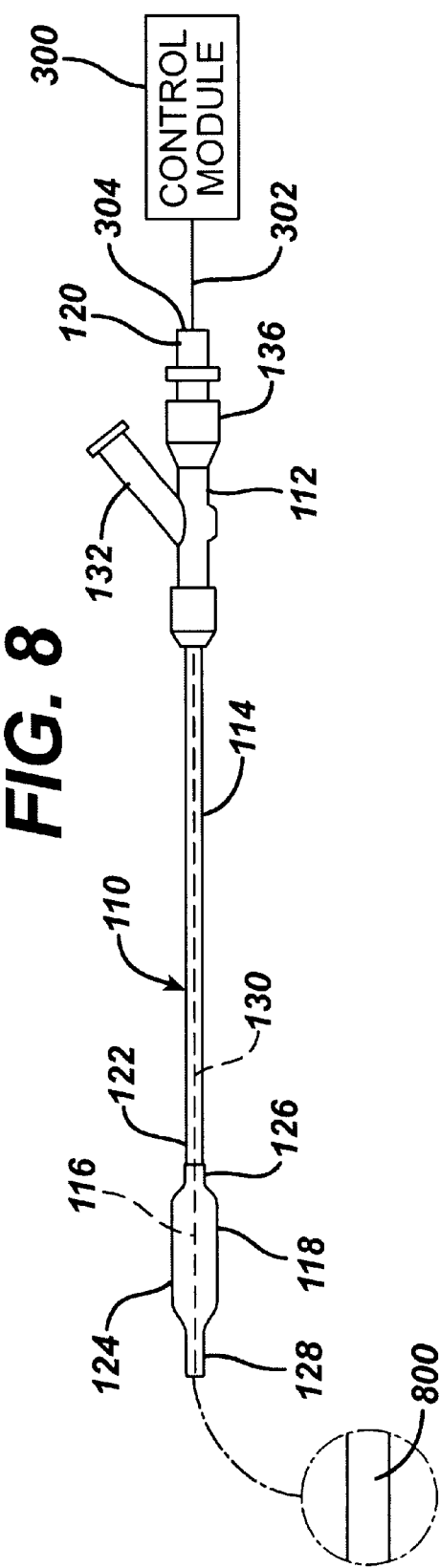
FIGS. 8 and 8A are perspective views of a seventh exemplary embodiment of the controllable intralumen medical device in accordance with the present invention.
Figure 8A:
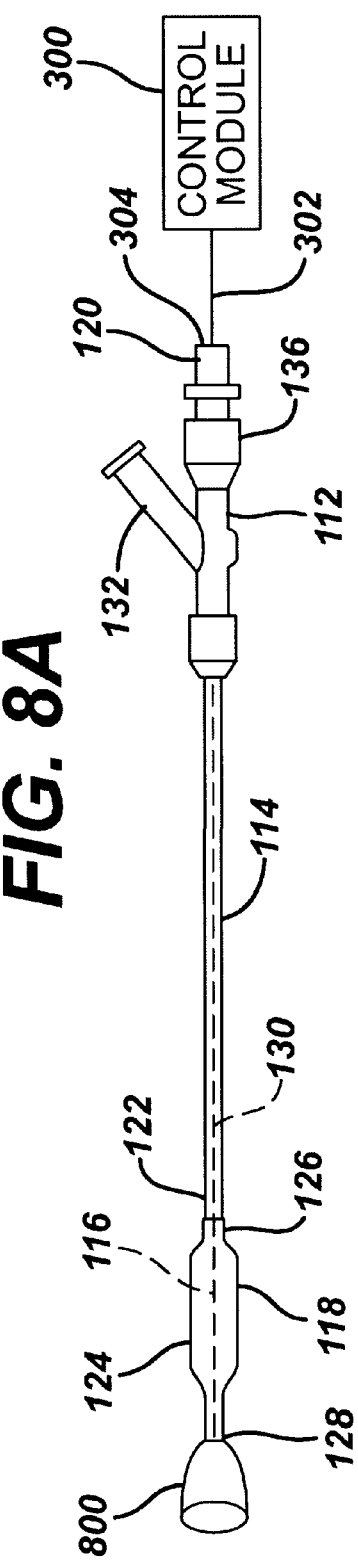

In yet another alternate embodiment, a tubular member may be formed from the composite. FIG. 8 illustrates a composite tubular member 800 attached to the end of the distal leg 128 utilizing any suitable means as discussed above. When no voltage is applied to the composite tubular member 800, the tubular composite member 800 remains at its normal relaxed diameter. When a predetermined voltage is applied, the tubular member expands as illustrated in FIG. 8A. In this configuration, the balloon catheter 110 may be utilized as a clot catcher or as a balloon. Any section of the outer tubular body 114 may also be replaced with tubular sections made from the composite material.

While the various exemplary embodiments described above have focused on the outer tubular member 114 and the distal end of the balloon 118, any sections or portions of the balloon catheter 110 may be configured as described above. For example, the balloon 118, which is also flexible, may incorporate the composite strands. Also, various combinations of the exemplary embodiments illustrated may be utilized in a single flexible probe and independently controlled via a single control module. In addition, by varying the geometric configuration of the composite strands, by varying the geometry of the composite strands themselves and by varying the placement of the composite strands on the flexible probe, essentially limitless configurations may be achieved. In order to facilitate the reconfiguration process, the probe and the composite strands may be configured as modular components which are easily positioned and repositioned.

Although the above discussions describe various substantially static configurations, the control module may be utilized to induce various levels of dynamic manipulation. As stated above, the displacement of the composite strips depend on the magnitude of the applied voltage and on the frequency of the applied voltage. Accordingly, by automatically controlling the magnitude, polarity and frequency of the applied voltage via the control module, as well as composite strip placement and geometry, the flexible probe device may be made to wiggle, slither, twirl, pulse, vibrate, rotate or virtually be made to make any other movement or combination of movements. The control module preferably comprises a closed loop control system, which may be implemented in hardware, software or a combination of hardware and software.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. A controllable intralumen medical device comprising:
   a flexible medical probe having one or more integral electroactive polymer actuators, the one or more integral electroactive polymer actuators are attached to the flexible medical probe at predetermined locations; and
   a control module coupled to the flexible medical probe for selectively controlling the one or more electroactive polymer actuators.

2. The controllable intralumen medical device according to claim 1, wherein the flexible medical probe comprises a catheter.

3. The controllable intralumen medical device according to claim 1, wherein the flexible medical probe comprises an endoscopic probe.

4. The controllable intralumen medical device according to claim 1, wherein the one or more integral electroactive polymer actuators are electrically coupled to the control module.

5. The controllable intralumen medical device according to claim 4, wherein the one or more integral electroactive polymer actuators comprise ion-exchange polymer-noble metal composites.

6. A method for controlling the movement of an intralumen medical device, comprising:

integrating one or more electroactive polymer actuators into the intralumen medical device at one or more predetermined locations; and selectively controlling the one or more electroactive polymer actuators to cause specific movements and states of rigidity in the intralumen medical device.

7. A controllable intralumen medical device comprising:

a flexible medical probe having one or more integral electroactive polymer actuators, the one or more integral electroactive polymer actuators replace one or more predetermined sections of the flexible medical probe; and a control module coupled to the flexible medical probe for selectively controlling the one or more electroactive polymer actuators.

* * * * *